US006376442B1

(12) United States Patent
Perthuisot et al.

(10) Patent No.: US 6,376,442 B1
(45) Date of Patent: Apr. 23, 2002

(54) LAVATORY CLEANSING BLOCK HAVING TWO FRAGRANCE REGIONS

(75) Inventors: Christophe Perthuisot, Rambouillet; Veronique Mathieu, Chartres, both of (FR)

(73) Assignee: Reckitt Benckiser France, Massy Cedex (FR)

( * ) Notice: Subject to any disclaimer, the term of this patent is extended or adjusted under 35 U.S.C. 154(b) by 0 days.

(21) Appl. No.: 09/600,926
(22) PCT Filed: Jan. 28, 1999
(86) PCT No.: PCT/GB99/00286
   § 371 Date: Aug. 30, 2000
   § 102(e) Date: Aug. 30, 2000
(87) PCT Pub. No.: WO99/38950
   PCT Pub. Date: Aug. 5, 1999

(30) Foreign Application Priority Data

Jan. 29, 1998 (EP) .............................. 98400188
Jul. 6, 1998 (GB) .............................. 9814445

(51) Int. Cl.[7] .............................. C11D 17/00
(52) U.S. Cl. .............. 510/191; 510/192; 510/101; 510/367; 510/447; 264/148; 264/241; 264/177.11

(58) Field of Search .................. 510/191, 101, 510/192, 367, 382, 392, 438, 439, 451, 447; 264/148, 177.11, 241

(56) References Cited

U.S. PATENT DOCUMENTS 4,683,072 A * 7/1987 Holdt et al. ............. 252/102
5,759,974 A * 6/1998 Menke et al. ............ 510/191

FOREIGN PATENT DOCUMENTS

WO    WO97/34993    9/1997    ........... C11D/17/00

OTHER PUBLICATIONS

Copy of GB Patent Office Search Report for GB 9814445.4 dated Sep. 22, 1998.

* cited by examiner

Primary Examiner—Necholus Ogden
(74) Attorney, Agent, or Firm—Fish & Richardson P.C.

(57) ABSTRACT

A lavatory cleansing block having a perceived approximately constant intensity of fragrance throughout the life of the block, which comprises an inner region having an inner fragrance and an outer region having an outer fragrance which is different from said inner fragrance. The inner fragrance is present in a concentration by weight which is less than or equal to 1.1 times the concentration of the outer fragrance.

11 Claims, 1 Drawing Sheet

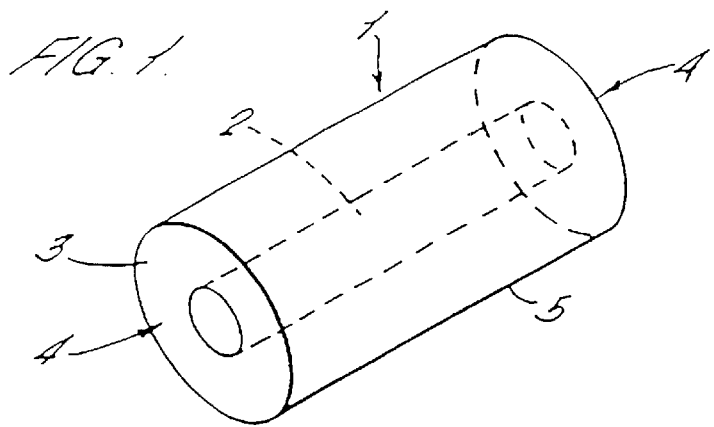
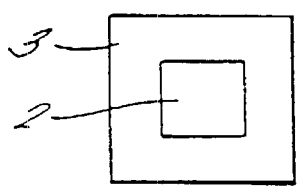
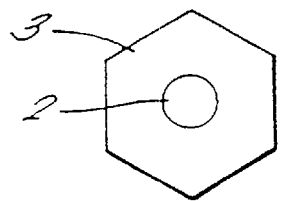
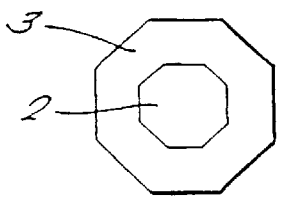
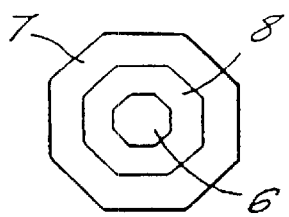
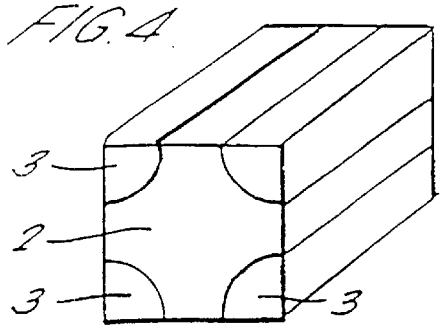

LAVATORY CLEANSING BLOCK HAVING TWO FRAGRANCE REGIONS

The present invention relates to lavatory cleansing blocks, their use and a method for their preparation.

BACKGROUND OF THE INVENTION

Solid lavatory cleansing blocks are well known in the art. Such blocks are typically designed to release active materials, including fragrance (or perfume), throughout their life. For example ITB (in the bowl) lavatory cleansing blocks are known which are hung from the rim of the lavatory bowl in a conventional container and which are designed to release fragrance and cleansing components upon dissolution of the block when the toilet is flushed. Additionally ITC (in the cistern) lavatory blocks are known for cleansing toilet systems; such block is placed in the cistern so that when the toilet is flushed cleansing components are released with the flush water into the toilet bowl.

Such lavatory cleansing blocks are conventionally based on a single homogenous formulation, which typically comprises a mixture of one or more bleaching agents, surfactants, fragrances and binders.

A disadvantage with such blocks is that a constant release of active materials throughout the life of the block cannot be achieved. The rate of release of an active material is linked not only to the concentration of the active material in the block but also to the size of the block. Thus a reduction in the surface area of the block during the life thereof will result in a reduction in the level of release of the active material.

WO 96/14392 (Henkel KG) discloses a cleanser in bar form for flush toilets, consisting of at least two different aggregates placed together, whereby one of the aggregates is at least partially enclosed by the other aggregate or aggregates, wherein the enclosed aggregate and at least one of the other aggregates contain at least a same active ingredient, whereby the concentration of at least one of these active ingredients in the enclosed aggregate is at least 1.3 times the concentration of the same active ingredient in the enclosing aggregate or aggregates.

The above active ingredient may be, for example, a perfume. Water penetrates into a lavatory block during use of the block. Towards the end of its life, a block may contain a significant proportion of water. Thus, in the case of the above block, the fragrance, which is the same in both regions of the block, will nevertheless not perform in the same way throughout the entire life of the block as the block absorbs more and more water. Furthermore it is known that the amount of fragrance contained in a formulations is key to determining the final rheology of the paste. If the same fragrance is present in two formulations in different amounts as in the above block, the rheologies may be vastly different such that co-extrusion of the two regions would be very difficult without readjusting the rheology of the two pastes.

SUMMARY OF THE INVENTION

We have now devised a block comprising at least two regions which is suitable for use as a lavatory cleanser and which allows active ingredients to be released from the block at a relatively constant rate over time in which the concentration of the fragrance in the inner region is not significantly greater than the concentration of the fragrance in the outer region. Since different fragrances are used in the inner and outer regions it is possible to use fragrances which take into account the problem of water penetration into the block. A fragrance can be used in the inner region which is more easily delivered from a wet block. Furthermore the rheologies of the inner and outer phases can be more easily controlled.

The present invention provides a lavatory cleansing block having a perceived approximately constant intensity of fragrance throughout the life of the block, which comprises an inner region comprising an inner fragrance and an outer region comprising an outer fragrance which is different from said inner fragrance, the inner fragrance being present in a concentration by weight which is less than or equal to 1.1 times the concentration of the outer fragrance.

The present invention also provides the use of a block as defined above as a lavatory cleansing block.

The present invention additionally provides a method of preparing a block as defined above which comprises extruding the inner region and outer region to form a solid block.

BRIEF DESCRIPTION OF THE DRAWINGS

In the attached drawings:

FIG. 1 is a schematic perspective view of a lavatory block of the present invention.

FIGS. 2a, 2b, 2c and 3 are schematic cross-sectional views of further blocks of the present invention.

FIG. 4 is a schematic perspective view of a further lavatory block of the present invention.

DETAILED DISCLOSURE

The block of the present invention may be used, for example, as an ITB or ITC block.

The block of the present invention may contain active materials of the usual type contained in lavatory cleansing blocks. Thus each region or all regions contain at least one of a surfactant, bleaching agent and anti-limescale agent. Each region may also comprise at least one other material such as a dye or colourant, preservative, binder, filler and/or solubility control agent.

Examples of surfactants are anionic, cationic and non-ionic surfactants. Examples of anionic surfactants are alkali metal salts of alkyl substituted benzene sulfonic acids, alkali metal salts of long chain fatty sulfates, alkali metal salts of long chain fatty sulfonates, alkali metal ether sulfates derived from alcohols and alkyl phenols, alkali metal sulfosuccinates and alkali metal sarcosinates. Examples of cationic surfactants are quaternary ammonium bromides and chlorides containing a long chain alkyl group such as benzalkonium chloride. Examples of non-ionic surfactants are those of the betaine or imidazoline types.

Examples of bleaching agents are solid halogen release agents such as alkali metal or alkaline earth metal hypochlorites, halogenated isocyanuric acid and alkali metal salts thereof and chlorinated dimethyl hydantoin. Peroxy and perborate compositions may be contemplated in appropriate formulations.

Examples of anti-limescale agents are phosphonates, phosphates, formates and citrates. The counter ion may be, for example, silver or zinc. Zeolites may also be used.

Examples of dyes and colourants are yellow colourants such as Solvent Yellow 98 from Hoechst or Solvent Blue 70 from BASF. The choice of colour is arbitrary and any suitable colourants known in the art may be used.

Examples of preservatives are IRGASAN DP 300 (trade mark) from Ciba Geigy or VENTOCIL IB (trade mark) from Zeneca.

Examples of binders are starch, starch derivatives, cellulose ethers and polyethylene glycol ethers.

Examples of fillers are sodium sulfate and silica.

The rate of dissolution of each region of the block may be controlled by the optional addition to these regions of at least one solubility control agent. Suitable solubility control agents usually include materials having a solubility which is lower than readily soluble components (principally surfactants) of the regions. Such solubility control agents may vary in nature from substantially wholly water-soluble materials to materials having a low solubility in water. The solubility control agent may be present in different amounts in the inner region and the outer region, and/or different solubility control agents may be present in the inner region and the outer region.

Examples of substantially insoluble solubility control agents are paradichlorobenzene, waxes such as beeswax, carnauba wax and petroleum waxes, long chain fatty acids and alcohols and esters thereof and fatty alkylamides. Solubility control agents of limited aqueous solubility may also be used; examples thereof are known to those skilled in the art. Typically these can include various non-ionic surfactants. Suitable solubility control agents are those which can withstand the conditions of manufacture of the block (for example the pressure and temperature used in an extrusion process).

The block of the present invention comprises at least an inner region and an outer region. The inner region is at least partially encapsulated by the outer region. There may be one or more inner regions and/or one or more outer regions. For example there may be one inner region and one, two three or four or more outer regions. Generally at least 50% of the surface area of the inner region is covered, preferably from 50% to 100%, more preferably from 65% to 90%, even more preferably from 68.5% to 88.5%. At least one intermediate region may, for example, be present between the inner region and the outer region. Further regions may, for example, be present inside the inner region or outside the outer region. The weight ratio of the inner region to the outer region is desirably 0.05:1 to 5:1, preferably 0.3:1 to 0.8:1, more preferably 0.45:1 to 0.7:1. If an intermediate region is present, the weight ratio of the intermediate region to the outer region is generally from 0:1 to 0.8:1, preferably from 0.47:1 to 0.667:1.

Each of the active ingredients may be present in the same or different concentrations in the different regions of the block depending on the effect desired.

For instance any of the active ingredients may be present in a greater or less concentration in the inner region than in the outer region. For a more constant rate of release of a particular active material, it should be present in a greater concentration in the inner region than in the outer region. Some ingredients may be present in both the inner and outer regions, or only in the inner region or only in the outer region. Thus the same or different active materials may be released at different stages of the block's use life, and the rate of release of each active material can be controlled.

The inner and outer regions of the block may, for example, contain the following proportions of ingredients. Apart from the fragrance the inner and outer regions may have the same or different formulations:

| Component | % by weight |
|---|---|
| Anionic surfactants | 0 to 70% |
| Cationic surfactants | 0 to 15% |
| Non-ionic surfactants | 0 to 20% |
| Bleaching agents | 0 to 30% |
| Anti-limescale agents | 0 to 20% |
| Dyes or colourants | 0 to 20% |
| Preservatives | 0 to 5% |
| Binders | 0 to 25% |
| Fillers | 0 to 50% |
| Fragrance | 1 to 30% |

In the block of the present invention it is possible to achieve a perceived approximately constant intensity of release of fragrance throughout the life of the block. The perception of the intensity of a particular fragrance depends on a number of factors, for example its concentration and its sensory properties. The sensory properties of a fragrance depend, for example, on its perception threshold and volatility. Usually a fragrance with a higher volatility and/or lower perception threshold will be considered to be more intense. Typically a fragrance is made up of a number of individual fragrance components. It is impossible to measure the intensity of a fragrance by a scientific method. Accordingly the intensity of a fragrance is measured by tests using consumers and/or panellists.

The intensity of a fragrance in a lavatory blocks can be measured by the following standard method.

Two sample lavatory blocks are taken and weighed. One of the blocks are then placed in a cage and placed on a rotating disk. The disk is rotated at 10 rpm under a water shower having a temperature of 30° C. The weight of the block is recorded regularly until it has lost 75% of the block weight. This generally takes about 90 minutes. At this stage the block consists only of the inner region since the entire outer region has been washed away. At the very end the second block is added, just to be wetted for 2 to 3 minutes.

The two blocks are left at room temperature for 1 hour. At the same time two olfaction cabins measuring 0.80×1.20× 2.60~2.5 $m^3$ and having placed therein a toilet bowl and cistern are ventilated for 1 hour. The ventilation is then stopped and the two blocks are disposed in separate cabins on the rim of the toilets. The toilets are flushed once and left in the cabin for 1 hour, following which a panel of 20 to 30 people are asked to evaluate the fragrancing strength by smelling through small window of each cabin. Each panel member indicates the cabin where the fragrance is strongest.

This method can quickly and simply show whether a lavatory block has a perceived approximately constant intensity of fragrance throughout the life of the block.

A block is considered to have perceived approximately constant intensity of fragrance throughout the life of the block if the following formula is met:

$|I-O| \leq 15$ wherein $I$ = percentage of panellists considering inner region has greatest intensity $O$ = percentage of panellists considering outer region has greatest intensity.

Preferably, $|I-O| \leq 10$, more preferably $\leq 7$.

Thus a block in which 42.5% of panellists consider that a block with no wear has the greatest fragrance and in which 57.5% of panellists consider that the block with 75 wt. % wear has the greatest fragrance, or vice versa, meets the requirement of perceived approximately constant intensity.

The scents of the fragrances in the inner and outer regions may be the same or different. The fragrances may, for example, be chosen to produce a substantially similar scent in the inner and outer regions, and in any other regions which may be present, in which case the block will have a substantially constant scent and intensity of scent throughout its life. The fragrances may also, for example, be chosen to produce different scents in the inner and outer regions, and in any other regions which may be present, in which case the block will have different scents at the beginning of its life and at the end of its life, but still have a substantially constant intensity of scent throughout its life. This may be useful to act as an indication to the consumer that the block has reached the end of its useful life.

In the present invention the concentration of a fragrance is to be understood as being the total concentration of the individual fragrance components within the fragrance. The solvent used, if any, is not included in the calculation unless it itself has a fragrance, ie it acts as an individual fragrance component. For example terpenes (for example of orange or lemon, or terpineol) and phenyl ethyl alcohol act as solvents, but have an olfactive impact and are therefore considered to be fragrance components in the context of the present invention. The concentration of a fragrance in a block can be measured by extracting the liquid in the block and analysing it. A suitable method is chromatography in which each raw material may be identified and quantified.

In general a fragrance is made up of a number of individual components, each of which has its own scent and intensity. The inner fragrance and the outer fragrance may have no individual components in common, or may have at least one individual component in common.

Thus there may be, for example, at least one individual component in common between the inner and outer fragrances. The individual components in common may make up, for example, up to 95 wt % of each fragrance. The relative concentrations of the individual components within the inner fragrance and the outer fragrance does not form an essential aspect of the present invention. Each of the individual components in common may be present in the inner and outer fragrances in substantially the same concentrations, or may be present in a greater concentration in either the inner fragrance or the outer fragrance.

Thus in a first embodiment of the present invention the outer fragrance consists of 100 wt % fragrance component A (wherein fragrance component A contains at least one individual fragrance). The inner fragrance consists of fragrance component A and fragrance component B (wherein fragrance component B is made up of at least one individual fragrance, none of which is present in fragrance component A). Fragrance component B provides a stronger scent. The inner fragrance may consist of, for example, at least 50 wt % fragrance component A, preferably at least 75 wt % fragrance component A, more preferably at least 90 wt % fragrance component A, even more preferably about 95 wt % fragrance component A, the balance being fragrance component B.

In a second embodiment of the present invention, the inner fragrance consists of fragrance components A and B (as defined in the first embodiment) and the outer fragrance consists of fragrance component A (as defined in the first embodiment) and fragrance component C (wherein fragrance component C is made up of at least one individual fragrance, none of which is present in fragrance components A or B). Fragrance component C may provide a more sophisticated scent, and is of a lesser intensity, than fragrance component B. The inner and outer fragrances may consist of, for example, at least 50 wt % fragrance component A, preferably at least 75 wt % fragrance component A, more preferably at least 90 wt % fragrance component A, even more preferably about 95 wt % fragrance component A, the balances being fragrance component B for the inner fragrance and fragrance component C for the outer fragrance.

In order to chose appropriate inner and outer fragrances for testing by consumers or panellists, an appropriate master fragrance may be prepared from individual fragrances. This master fragrance may be used, for example, as the outer fragrance. One or more further individual fragrances may then be added to form the inner fragrance. If desired, one or more individual fragrances may also be removed to modify the scent of the outer fragrance. It is possible, for example, to add individual fragrances to form the inner fragrance which are perceptually similar to the individual fragrances removed to form the outer fragrance. Another possibility is to prepare a master fragrance and add one or more individual fragrances to it to form the inner fragrance and one or more different individual fragrances to it to form the outer fragrance. The consumers or panellists may test the pairs of inner and outer fragrances throughout this procedure in order to arrive at an appropriate pair of fragrances with approximately the same intensities.

The inner fragrance is present in the inner region of the block of the present invention in a concentration which is less than or equal to 1.1 times the concentration of the outer fragrance in the outer region. In one embodiment the inner fragrance is present in a concentration which is less than or equal to the concentration of the outer fragrance, for example in a concentration of 0.75 to 1.0 times, preferably 0.8 to 0.9 times, the concentration of the outer fragrance. In another embodiment the concentration of the inner fragrance is approximately equal to the concentration of the outer fragrance, for example from 0.95 to 1.05, preferably 0.98 to 1.02, the concentration of the outer fragrance.

The concentration of the inner fragrance is, for example, from 1 to 30 wt %, preferably from 7 to 30 wt %, more preferably from 7 to 15 wt %, based on the total weight of the inner region. The concentration of the outer fragrance is, for example, from 1 to 30 wt %, preferably from 7 to 30 wt %, more preferably from 7 to 15 wt %, based on the total weight of the outer region.

The inner and outer fragrances, and the individual fragrances thereof, may be used in the absence or presence of a solvent. As indicated above, the concentrations and relative amounts of the various fragrances mentioned herein do not include the solvent. A solvent is in general used. Suitable solvents include those generally used for fragrances, such as ketones, alcohols and ethers. These solvents are known to those skilled in the art.

The block of the present invention may be prepared, for example, by extrusion. Formulations for the different regions may be extruded to form a rod or bar which is then cut into appropriately sized pieces or blocks.

Suitably the ingredients of each formulation are fed into separate screw-mixer-extruders. In each mixer the ingredients are conveyed to the inside of the barrel by the rotation of the screws. Each different formulation is then pushed outside its respective barrel towards the compression chamber. In this chamber the different formulations can be joined to each other. For example, the different formulations can exit the die one inside another, which is so called axial extrusion.

Preferably two formulations are fed into two separate twin-screw-mixer-extruders, and the two formulations are joined to each other by axial co-extrusion.

For a better understanding of the invention, and to show how the invention may be put into effect, reference will be made to the drawings.

Referring to FIG. 1, there is illustrated a lavatory block of generally cylindrical shape. The block includes an inner region 2 and an outer region 3. The block is preferably formed by co-extrusion of differing formulations by means known in the art, such as the screw-mixer-extruders mentioned above. Inner region 2 comprises the inner fragrance and outer region 3 comprises the outer fragrance. Thus a substantially constant intensity (ie release) of fragrance may be perceived by the consumer throughout a major portion, or substantially all, of the use life of the block. The fragrances in the inner region 2 and the outer region 3 may have substantially the same or different scents.

Inner region 2 may also comprise a formulation including at least one different active ingredient (for example a bleach or dye) from the formulation of outer region 3. Alternatively the inner region 2 may comprise a formulation including the same active ingredients as those in outer region 3, either at the same or different concentrations.

In a preferred embodiment of the present invention inner region 2 comprises a formulation including at least one active ingredient at a higher concentration than the same active ingredient in the formulation of outer region 3. For example inner region 2 may comprise a dye at a higher concentration than the dye in outer region 3, or inner region 2 may contain a different dye from that in outer region 3. When inner region 2 comprises a higher level of dye than that in outer region 3 it is possible to achieve a substantially constant level of dissolution of dye into the flush water of the lavatory throughout a major portion, or substantially all, of the use life of the block. When regions 2 and 3 comprise different dyes, an end of life indicator may be provided when outer region 3 is substantially completely dissolved and the dye of inner region 2 predominates.

In the extrusion process for the formation of blocks, the formulations of regions 2 and 3 are co-extruded from the extrusion die to form a bar or rod. The bar or rod is then cut substantially perpendicularly to its major axis to form individual blocks with end faces 4. In use outer region 3 is, at least initially, exposed to the flush water of the lavatory at end faces 4 and outer surface 5 whereas inner region 2 is exposed to flush water, at least initially, only at end faces 4. It can thus be seen that by appropriate selection of the relative thicknesses of regions 2 and 3, inner region 2 may be exposed to the flush water to only a minor extent until a significant or substantial portion of outer region 3 has been dissolved away. A person skilled in the art is able to select the relative thicknesses of regions 2 and 3 in order to achieve desired respective rates of dissolution of the regions 2 and 3 and thereby to achieve desired rates of release of active ingredients and fragrances contained in these regions.

The rate of dissolution of the regions 2 and 3 may also be controlled by the optional addition to the formulations of these regions of solubility control agents.

By means of the extrusion process, blocks of the present invention may be produced in a variety of shapes. Examples of shapes are illustrated in FIGS. 2a, 2b and 2c, which show rectangular or square, hexagonal and octagonal cross sections. Other shapes, which may be selected in accordance with their functional and/or aesthetic qualities, may be chosen by those skilled in the art. In FIGS. 2a, 2b and 2c, reference numeral 2 is used to indicate the inner region and reference numeral 3 is used to indicate the outer region.

In FIG. 3 there is illustrated a block including an inner region 6, an outer region 7 and an intermediate region 8. The regions 6, 7 and 8 may include different active ingredients or may include the same active ingredients at different concentrations. For example inner region 6 may include a dye at a higher concentration than in intermediate region 8 which in turn includes the dye at a higher concentration than in outer region 7. Such a construction provides an even more constant release of active ingredient through the use life of the block. In an alternative construction according to FIG. 3, intermediate region 8 may provide a barrier layer between two incompatible components. Thus one incompatible component may be provided in inner region 6 and another incompatible component may be provided in outer region 7. Diffusion of one incompatible component into the other is prevented by intermediate region 8. Examples of incompatible components which may be provided in the separated regions 6 and 7 include bleaching agents and some fragrances and/or dyes, where the bleaching agent may react chemically with the fragrance or dye resulting in a loss or change in scent or colour.

In FIG. 4 there is illustrated a lavatory block of generally square cross section. The block includes an inner region 2 and four quarter circular outer regions 3 forming a star-in-a-square pattern. The block may be, for example, about 24 mm×24 mm×60 mm, with the radius of each corner quarter circle being about 11 mm. The block is preferably formed by co-extrusion as mentioned above.

The present invention is now further described in the following Examples.

EXAMPLE 1

A pair of citrus fragrances, ie an inner fragrance and an outer fragrance, were prepared by mixing the following individual components in the amounts indicated. The amounts are all given in parts by weight.

TABLE 1

| Individual Fragrance | Outer | Inner |
|---|---|---|
| Decanal | 80 | 80 |
| Citral | 80 | 80 |
| Orange Terpenes | 100 | 100 |
| Dihydromyrcenol | 250 | 200 |
| Cyclacet | 20 | 20 |
| Allyl Amyl Glycolate | 8 | 8 |
| Methyl dehydro Jasmonate | 155 | 150 |
| Methyl Nonyl Acetaldehyde |  | 10 |
| Grapefruit Essential Oil |  | 280 |
| Lemon Terpenes | 280 |  |
| Methyl Pamplemousse |  | 6 |
| Isobornyl Acetate |  | 62 |
| Basil Essential Oil | 7 |  |
| Galbanum Essential Oil | 10 |  |
| Rhubofuran |  | 1 |
| Stemone |  | 3 |
| Citronellol | 10 |  |
| TOTALS: | 1000 | 1000 |

EXAMPLE 2

A pair of fragrances, ie an inner fragrance and an outer fragrance, were prepared by mixing the following individual components in the amounts indicated. The weights are all given in parts by weight.

TABLE 2

| Individual Fragrance | Outer | Inner |
|---|---|---|
| Benzyl Acetate | 5.0 | 4.0 |
| Citronellol | 12.0 | 10.0 |
| Fruit Complex TG | 12.0 | 7.0 |
| Geranium Synthetic | — | 3.0 |
| Hexyl Cinnamic Aldehyde | 10.0 | 10.0 |
| Jasmacyclene/Verdyl Acetate | 12.0 | 10.0 |
| Jasmopyrane Forte | — | 10.0 |
| Jasmin Synthetic TG | 4.0 | 3.0 |
| Linalol | 10.0 | 6.0 |
| Methyl Ionone Gamma | 5.0 | 5.0 |
| Phenyl Ethyl Alcohol | 10.0 | 10.0 |
| Rose Synthetic TG | 8.0 | 5.0 |
| Terpineol | 12.0 | 12.0 |
| Boisvelone/Iso E Super | — | 5.0 |
| TOTALS: | 100.0 | 100.0 |

EXAMPLE 3

A pair of rose fragrances, ie an inner fragrance and an outer fragrance, were prepared by mixing the following individual components in the amounts indicated. The weights are all given in parts by weight.

TABLE 3

| Outer | | Inner | |
|---|---|---|---|
| Aldehyde C-10 Decyl | 2.00 | Aldehyde C-11 Undecylenic | 1.50 |
| Aldehyde C-12 MNA | 0.50 | Aldehyde C-9 Nonylanic | 1.00 |
| Eugenal | 4.00 | Citronellol | 17.50 |
| Phenyl Ethyl Alcohol | 22.50 | Rose Oxide | 1.00 |
| Citronellol | 20.00 | Cedarwood | 7.00 |
| Sandalore | 2.00 | Euganol | 3.00 |
| Tricyclal | 1.00 | Phenyl Ethyl Alcohol | 22.50 |
| TOTALS: | 52.00 | | 53.50 |

EXAMPLE 4

A pair of muguet fragrances, ie an inner fragrance and an outer fragrance, were prepared by mixing the following individual components in the amounts indicated. The amounts are all given in parts by weight.

TABLE 4

| Outer | | Inner | |
|---|---|---|---|
| Aldehyde C-11 Undecylenic | 1.00 | Aldehyde C-12 MNA | 1.00 |
| Aldehyde C-10 decyl | 1.00 | Lillal | 10.00 |
| Hydroxycitronellal | 10.00 | Rosalva | 1.00 |
| Citronellol | 20.00 | Nerol | 20.00 |
| Skatole 10% DPG | 1.00 | Indole 10% DEP | 1.00 |
| Phenyl ethyl alcohol | 45.00 | Geraniol | 45.00 |
| Cedar wood oil virg. | 10.00 | Sandalwood oil | 10.00 |
| Cyclogalbanate | 2.00 | Tricyclal | 2.00 |
| Vanillin | 5.00 | Ethyl Vanillin | 5.00 |
| Eugenol | 5.00 | Methyl Cinnamate | 5.00 |
| TOTALS: | 100.00 | | 100.00 |

Skatole 10% DPG = skatole containing 10% of dipropylene glycol (a solvent)

Indole 10% DEP = indole containing 10% of diethylene phthalate (a solvent)

EXAMPLE 5

A pair of lemon fragrance, i.e. an inner and an outer fragrance, were prepared by mixing the following individual components in the amounts indicated. The amounts are all given in parts by weight.

TABLE 5

| Outer | | Inner | |
|---|---|---|---|
| Aldehyde C 8 | 40 | Aldehyde C 8 | 40 |
| Aldehyde C 10 | 40 | Aldehyde C 10 | 40 |
| Aldehyde MNA | 10 | Aldehyde MOA | 20 |
| Citral pure | 100 | Litsea Cubeba | 150 |
| Geranyl nitrile | 50 | Geranyl nitrile | 50 |
| Citronella oil | 300 | Citronellal | 384 |
| Orange oil | 50 | Orange terpenes | 100 |
| Geraniol | 100 | Citronellol | 130 |
| Diphenyl oxide | 20 | Diphenyl methane | 30 |
| Benzyl Salicylate | 30 | Benzyl Salicylate | 30 |
| Beta Ionone | 5 | Alpha Ionone | 10 |
| Methyl Ionone | 10 | Methyl Ionone | 10 |
| Tonalide | 70 | Galaxolide | 100 |
| Hexyl cinnamic ald. | 175 | Aldehyde C6 | 1 |
| | | Tridecen nitrile | 2 |
| | | Dimethyl heptanol | 2 |
| | | Rose oxide | 1 |
| Total | 1000 | Total | 1100 |

EXAMPLE 6

Lavatory cleaning blocks were prepared from the following compositions:

| Inner region | | Outer region | |
|---|---|---|---|
| Block A | | | |
| Sodium alkyl aryl sulfonate | 25 wt % | Sodium alkyl aryl sulfonate | 50 wt % |
| Sodium α-olefin sulfonate | 20 wt % | Sodium sulfonate | 26 wt % |
| Sodium lauryl sulfate | 5 wt % | Sodium citrate | 8 wt % |
| Sodium sulfate | 26 wt % | Silica | 6 wt % |
| Sodium citrate | 8 wt % | Outer lemon fragrance of Example 5 | 10 wt % |
| Silica | 6 wt % | | |
| Inner lemon fragrance of Example 5 | 10 wt % | | |
| Block B | | | |
| Sodium alkyl aryl sulfonate | 20 wt % | Sodium α-olefin sulfonate | 60 wt % |
| Sodium α-olefin sulfonate | 35 wt % | Sodium sulfate | 26 wt % |
| Sodium lauryl sulfate | 10 wt % | Sodium citrate | 6 wt % |
| Sodium sulfate | 27 wt % | Silica | 2 wt % |
| Silica | 2 wt % | Outer lemon fragrance of Example 5 | 6 wt % |
| Inner lemon fragrance of Example 5 | 6 wt % | | |

To prepare each block the inner and outer regions were co-extruded to form a rod or bar, which was then cut into appropriately sized pieces or blocks.

What is claimed is:

1. A lavatory cleansing block having a perceived approximately constant intensity of fragrance throughout the life of the block, which comprises an inner region comprising an inner fragrance and an outer region comprising an outer fragrance which is different from said inner fragrance, the inner fragrance being present in a concentration by weight which is less than or equal to 1.1 times the concentration of the outer fragrance.

2. A block according to claim 1 wherein the inner and outer regions are concentric.

3. A block according to claim 1 which has a square cross section and which comprises one inner region and four quarter circular outer regions forming a star-in-a-square pattern.

4. A block according to claim 1 wherein the inner fragrance is present in a concentration which is less than or equal to the concentration of the outer fragrance.

5. A block according to claim 4 wherein the inner fragrance is presenting a concentration which is approximately equal to the concentration of the outer fragrance.

6. A block according to claim 1 wherein the inner fragrance and the outer fragrance have the same scent.

7. A block according to claim 1 wherein the concentration of the inner fragrance is from 7 to 15 wt % based on the total weight of the inner region.

8. A block according to claim 1 wherein the inner and outer fragrances have at least one individual fragrance component in common.

9. A block according to claim 1 wherein the inner and outer fragrances have at least one individual fragrance component in common.

10. A block according to claim 9 wherein all of the components in common between the inner and outer fragrances are present in the inner fragrance in a concentration by weight which is less than or equal to the concentration thereof in the outer fragrance.

11. A method of preparing a block as defined in claim 1 which comprises extruding the inner layer and outer layer to form a solid block.

* * * * *

UNITED STATES PATENT AND TRADEMARK OFFICE
CERTIFICATE OF CORRECTION

PATENT NO.   : 6,376,442 B1  
DATED        : April 23, 2002  
INVENTOR(S)  : Christophe Perthuisot and Véronique Mathieu It is certified that error appears in the above-identified patent and that said Letters Patent is hereby corrected as shown below:

Column 11,  
Line 20, "presenting" should be -- present in --

Column 12,  
Line 6, insert claim 8,  
-- A block according to claim 1 wherein the concentration of the outer fragrance is from 7 to 15 wt% based on the total weight of the outer region. --  
Line 6, existing Claim 8 should become Claim 9.  
Lines 9-11, existing Claim 9 should be deleted.

Signed and Sealed this

Eighteenth Day of March, 2003

JAMES E. ROGAN  
*Director of the United States Patent and Trademark Office*